(12) United States Patent
Casale et al.

(10) Patent No.: US 7,737,415 B2
(45) Date of Patent: Jun. 15, 2010

(54) SYSTEM FOR THE CONTROL, VERIFICATION AND RECORDING OF THE PERFORMANCE OF A RADIOISOTOPE GENERATOR'S OPERATIONS

(75) Inventors: Guillermo Arturo Casale, Buenos Aires (AR); Jorge Osvaldo Nicolini, Buenos Aires (AR); Elvira Calvo Kock, New York, NY (US)

(73) Assignee: Laboratorios Bacon, S.A., Province of Buenos Aires (AR)

( * ) Notice: Subject to any disclaimer, the term of this patent is extended or adjusted under 35 U.S.C. 154(b) by 999 days.

(21) Appl. No.: 10/586,755

(22) PCT Filed: Jan. 27, 2004

(86) PCT No.: PCT/US2004/002073

§ 371 (c)(1),
(2), (4) Date: Jul. 20, 2006

(87) PCT Pub. No.: WO2005/083393

PCT Pub. Date: Sep. 9, 2005

(65) Prior Publication Data

US 2008/0149847 A1 Jun. 26, 2008

(51) Int. Cl.
*B01D 59/44* (2006.01)
(52) U.S. Cl. .............................. 250/432 PD
(58) Field of Classification Search ............... 324/71.1, 324/71.3, 71.4; 423/1, 2, 3, 6, 7, 62; 250/423 R, 250/428, 430, 431, 432 R, 433, 434, 435, 250/436, 437, 438, 432 PD
See application file for complete search history.

(56) References Cited

U.S. PATENT DOCUMENTS

| 4,280,053 | A | | 7/1981 | Evans et al. |
| 4,288,424 | A | * | 9/1981 | Neirinckx et al. ............ 424/1.61 |
| 4,625,118 | A | * | 11/1986 | Kriwetz et al. ......... 250/432 PD |
| 4,782,231 | A | | 11/1988 | Svoboda et al. |
| 4,837,110 | A | | 6/1989 | Kuhlmann et al. |
| 4,853,546 | A | * | 8/1989 | Abe et al. .............. 250/432 PD |
| 5,371,372 | A | * | 12/1994 | Phillips .................. 250/432 R |
| 5,774,782 | A | | 6/1998 | Mirzadeh et al. |
| 6,157,036 | A | * | 12/2000 | Whiting et al. ........ 250/432 PD |
| 6,267,717 | B1 | * | 7/2001 | Stoll et al. ..................... 600/4 |
| 6,972,414 | B2 | * | 12/2005 | Egorov et al. ......... 250/432 PD |
| 2003/0139640 | A1 | * | 7/2003 | Whittacre et al. .............. 600/1 |

* cited by examiner

*Primary Examiner*—David A Vanore
*Assistant Examiner*—Nicole Ippolito Rausch
(74) *Attorney, Agent, or Firm*—Egbert Law Offices PLLC

(57) ABSTRACT

This invention is referred to a digital technetium Tc-99m generator obtained by incorporating devices to allow the control, verification and recording of all the operations performed by the generator. The invention includes a conventional traditional generator Mo-99/Tc-99m, using either a dry or wet column, such as the ones commercially available for use in nuclear medicine. The invention also includes an electronic sensor of elution; an eluted activity measurement sensor; and a device to measure the nuclear quality of the eluted Tc-99m. There is an electronic memory with information for the user regarding: Generator No., Lot No., activity, calibration and expiration dates. The invention also includes a communication interface, whether via RS232, USB, parallel Port or any other input-output port of a PC; a control, and user interface software.

22 Claims, 5 Drawing Sheets

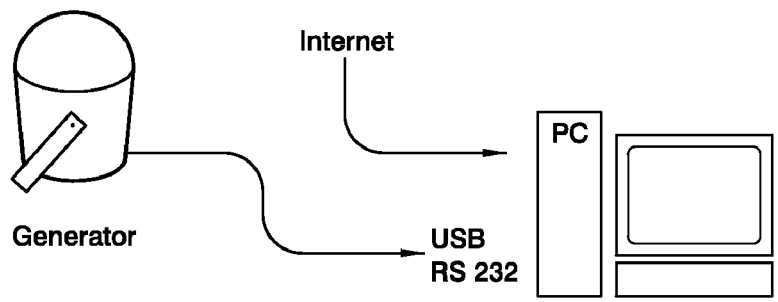
Fig. 1 CONNECTION
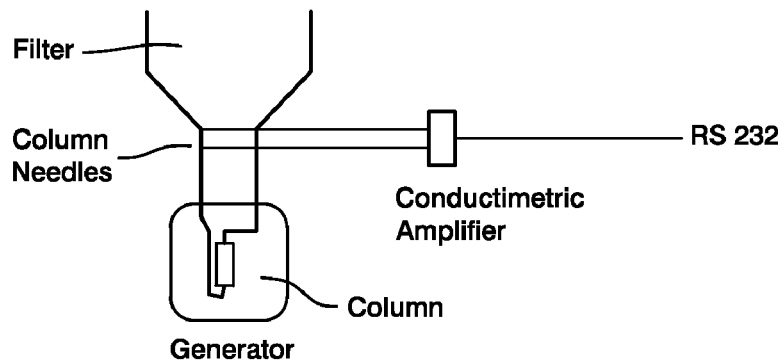
Fig. 2 HIGH FREQUENCY CONDUCTIMETRY
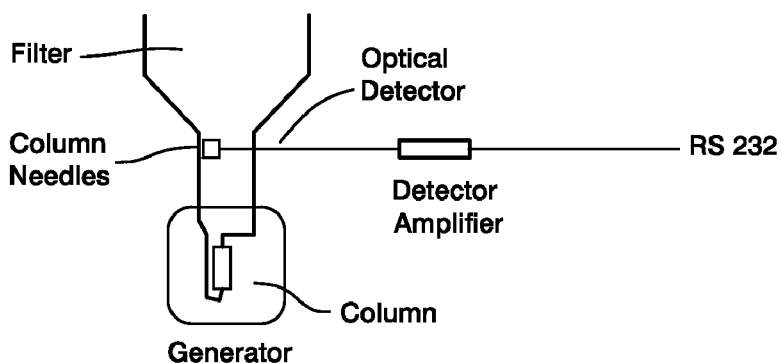
Fig. 3 PHOTOMETRY

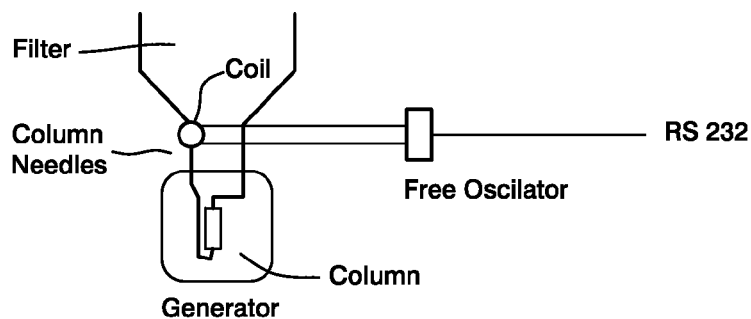
Fig. 4  IMPEDANCEOMETRY
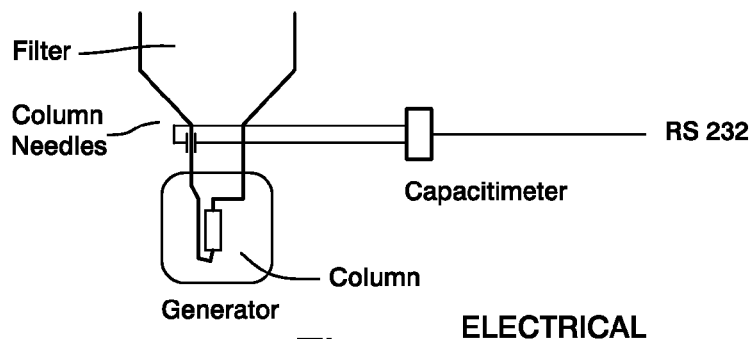
Fig. 5  ELECTRICAL CAPACITOMETRY
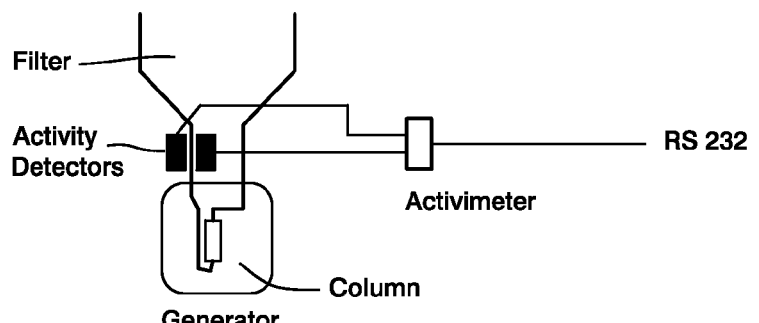
Fig. 6  EMITTED RADIATION DETECTION
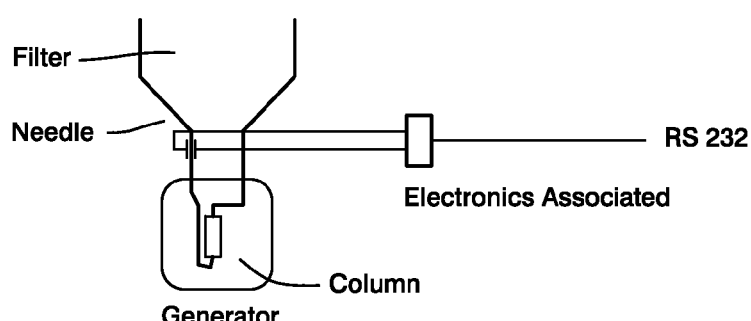
Fig. 7  MAGNETIC-HYDRODYNAMIC

ELECTRONIC CIRCUITS

| Port RS 232 | | | | Paralel |
|---|---|---|---|---|
| Name | Function | DB9 n° pin | DB25 n° pin | N° pin |
| DCD | In | 1 | 8 | 11 |
| RXD | In | 2 | 3 | 12 |
| TXD | Out | 3 | 2 | 2 |
| DTR | Out | 4 | 20 | 3 |
| GND | 0 volt | 5 | 7 | 25 |
| DSR | In | 6 | 6 | 13 |
| RTS | Out | 7 | 4 | 4 |
| CTS | In | 8 | 5 | 14 |
| RI | In | 9 | 22 | 15 |

Q1 type NPN BC547
R1 100 K
R2 700 K

Q1 type NPN BC547
R1 100 K
R2 700 K

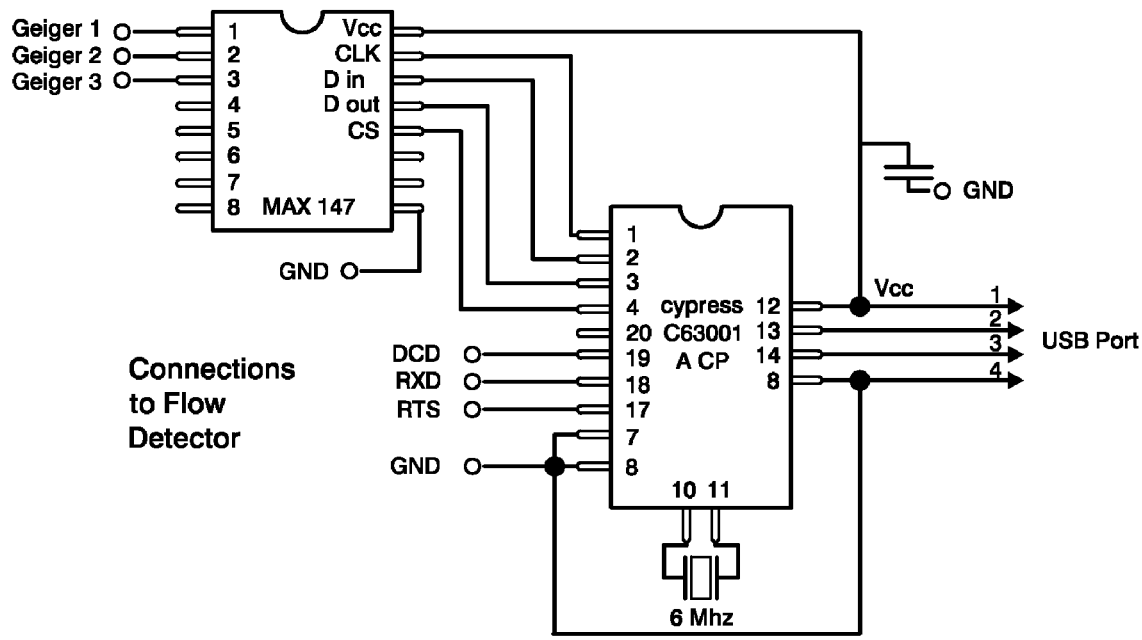
Fig. 12
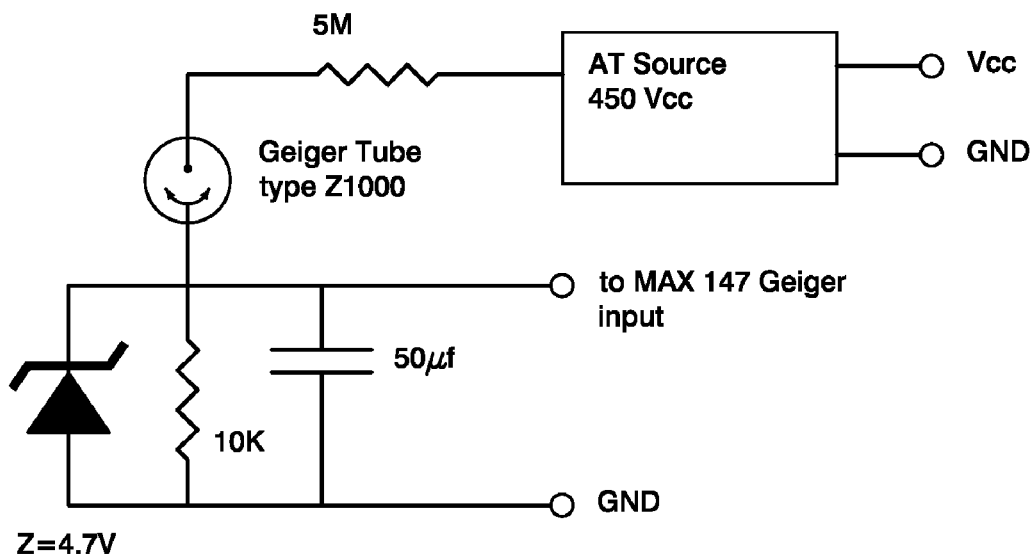
Fig. 13    CIRCUIT 6

SYSTEM FOR THE CONTROL, VERIFICATION AND RECORDING OF THE PERFORMANCE OF A RADIOISOTOPE GENERATOR'S OPERATIONS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

This invention relates to a system that allows the control, verification and recording (logging) of the performance of all operations carried out by a radioisotope generator. Such system comprises one or more sensors connected to an electronic device for data processing to provide performance control of a radioisotope generator, such as a Mo-99/Tc-99m Generator. In particular, the invention refers to a digitalized system for the measurement, verification and logging of all the operations performed by a Mo-99/-Tc-99m generator, including an electronic sensor of the elution of the generator, an eluted activity measurement device, a nuclear quality control device for Tc-99m, a communication interface to an electronic data processor and an user interface program.

2. Description of Related Art Including Information Disclosed Under 37 CFR 1.97 and 37 CFR 1.98.

Although technical bibliography and literature provides for a great variety of Tc-99m generators, there is no knowledge of digital generators, including digitalized equipment to control, verify and log every operation performed by the generator through a simple and economical means, such as a conventional computer connected to suitable means of sensing and with the appropriate software to process the information obtained through such sensors.

For example, improvements may be cited that comprise the generator of Technetium disclosed in the U.S. Pat. No. 5,774,782 referred to a $^{99}$Mo/$^{99m}$Tc generator system, including a sorbent column loaded with a composition containing $^{99}$Mo. The sorbent column has an effluent end in fluid communication with an anion-exchange column for concentrating $^{99m}$Tc eluted from the sorbent column. A method of preparing a concentrated solution of $^{99m}$Tc includes the general steps of:

a. providing a sorbent column loaded with a composition containing $^{99}$Mo, the sorbent column having an effluent end in fluid communication with an anion-exchange column;

b. eluting the sorbent column with a salt solution to elute $^{99m}$Tc from the sorbent and to trap and concentrate the eluted $^{99m}$Tc on the ion-exchange column; and c. eluting the concentrated $^{99m}$Tc from the ion-exchange column with a solution comprising a reductive complexing agent.

Moreover, U.S. Pat. No. 4,782,231 discloses a standard component $^{99m}$TC elution generator useful for medical purposes and consisting of prefabricated component parts. The main generator column of the device may be used both as an irradiation container and an elution container, enabling the user to supply activated or non-activated parts. The main generator column, made from neutrons, as little activatable materials, serves first as a reactor irradiation ampoule, and, after having been activated in the reactor by neutrons and after a simple adjustment, the main generator column simply serves directly as the generator column. It is filled with water insoluble molybdates or polymolybdates (with the molybdenum content in the range 10-40%), easily releasing $^{99m}$TC generated by radioactive decay of the mother $^{99}$Mo formed in it by neutron activation. This column filling serves originally as target material for reactor irradiations, and afterwards, it is directly used as the generator elution matrix.

U.S. Pat. No. 4,837,110 discloses a technetium-99m generator, its preparation and its use, wherein silica gels modified with amino groups or magnesium silicates are suitable carrier materials for technetium-99m generators since they retain copper(II) ions well and thus produce a copper-free elute.

U.S. Pat. No. 4,280,053 describes a Technetium-99m generator, that has a matrix having a compound of molybdenum-99 bound into or forming the matrix, the compound of the molybdenum-99 being substantially insoluble in an eluant, which can be used in a radiopharmaceutical and the molybdenum compound permitting diffusion of technetium-99m therethrough and elution therefrom. The molybdenum compound, which can be a monomolybdate, an isopolymolybdate or a heteropolymolybdate and zirconium molybdate, is preferred, although other cation molybdates may be used. Methods of preparation of the generator include dissolving irradiated molybdenum trioxide in alkaline solution and precipitating the molybdate at a selected pH and packing the precipitate in a finely divided form into a column.

None of the above mentioned generators embrace apiece of equipment like, the one described below, including novel features and performing new functions.

The proposed system of this invention, when incorporated to a radioisotope generator, substantially enhances its general usefulness and mainly adds previously unknown features.

BRIEF SUMMARY OF THE INVENTION

Summarizing, this invention refers to a digital technetium Tc-99m generator obtained by incorporating devices to allow the control, verification and recording of all the operations performed by the generator. The system includes:

a conventional traditional generator Mo-99/Tc-99m, using either a dry or wet column, such as the ones commercially available for use in nuclear medicine;

an electronic sensor of elution;

an eluted activity measurement sensor;

a device to measure the nuclear quality of the eluted Tc-99m, wherein nuclear quality refers to the level of radioactivity achieved or wanted;

an electronic memory means with information to the user, such as generator number, lot number, activity, calibration and expiration dates;

a communication interface, whether via RS232; USB, parallel port or any other input-output port of a PC; and a control and user interface software.

The applicability of these improvements provides the following advantages:

- it allows the user to know the activity available in the generator at any given time without having to resort to tables or to recall the last elution conducted on the generator, especially when generator elutions are conducted by more than one technical person;
- it automatically logs the day and hour of elution, saving it in an electronic file;
- it records the eluted activity and the identification of the operator;
- it automatically measures the activity of the eluted Tc-99m and determines its nuclear purity ($\mu$Ci Mo-99 per mCi Tc-99m);
- it computes the specific activity of Tc-99m which is important to determine the suitability of an eluate for labeling some radiopharmaceuticals, such as ECD and others known to those skilled in the art;
- in the case of the dry Mo-99/Tc-99m generator, the information regarding the residual humidity of the generator is fundamental to secure the next elution, since the elution performance drops drastically in case the generator remains "wet". The system guides the user to resolve the problem. If the user fails to log the solution, the producer may remotely access the data and call the user to help in resolving the problem;
- the log system records the operations conducted on all the generators for the operator's review;
- the log system allows conducting statistical analysis on the use of Tc-99m by the nuclear medicine unit; and
- the software, herein called "watchdog", is an integral part of this invention and alerts the operator in case of possible unauthorized elutions.

These are only some of the significant advantages of the present invention, that will become apparent upon reading the following description and upon reference to the enclosed drawings.

BRIEF DESCRIPTION OF THE SEVERAL VIEWS OF THE DRAWINGS

FIG. 1 is a schematic view of the generator's connection to the PC, either directly or through a port RS232, USB, parallel port, etc.

FIG. 2 shows a schematic view of an embodiment of the proposed elution detection sensor, wherein the elution detection is conducted by conductometry, which is based on the measurement of the electrical resistance of a portion of a metal tubing through which the physiological solution or the elution passes.

FIG. 3 is another schematic view of another embodiment, wherein the sensor detects the elution by measuring the changes in the intensity of a light beam which passes through a translucid section of the elution tubing.

FIG. 4 is a schematic view of still another embodiment, wherein the sensor detects the elution by impedanceometry based on measuring the changes in the frequency of a free oscillator.

FIG. 5 shows a schematic view of another embodiment, wherein the sensor detects the elution by measuring the changes in capacity in the elution as the eluate flows through the elution tubing.

FIG. 6 shows a schematic view of a further embodiment, wherein the sensor detects the elution by measuring the changes in radioactivity emitted by the eluate as it passes through the elution tubing.

FIG. 7 shows another schematic view of an embodiment, wherein the sensor detects the elution based on the magnethydrodynamic principle, i.e. the measurement of the weak orthogonal electric field created to the magnetic field applied to the elution tubing.

FIG. 12 shows a schematic view of circuit number 5 for the RadioFarma Elutec II system.

FIG. 13 shows a schematic view of circuit number 6 for the RadioFarma Elutec III.

DETAILED DESCRIPTION OF THE INVENTION

Figure 8:
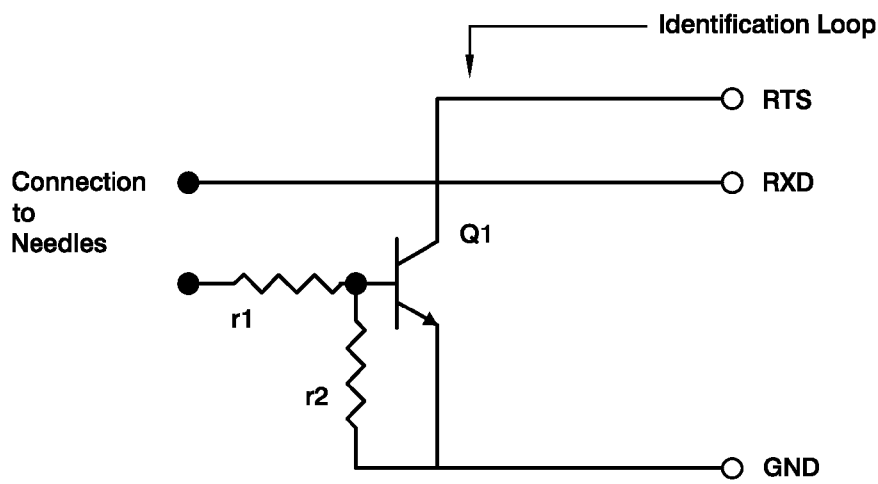
FIG. 8 shows a schematic view of a circuit number 1 of the identification loop for delivering information to the program in the circuit, that is connected to the port.

This invention refers to a system that, when incorporated into a radioisotope generator, performs certain operations, which enhances general usefulness of the system. The systems comprises:
- a conventional traditional generator of Mo-99/Tc-99m, using either a dry or wet column, such as the ones that have been commercially available for over 40 years in nuclear medicine;
- an electronic sensor of elution;
- an eluted activity measurement sensor;
- a device to measure the nuclear quality of the eluted Tc-99m;
- an electronic memory with information for the user, regarding: generator number, lot number, activity, calibration and expiration dates;
- a communication interface via RS 232, USB, parallel port or any other input-output port of a PC, wherein PC is understood to be a desktop PC, notebook PC, palm PC, and any other electronic and processing information device; and
- control and user interface software.

This system has the capability to provide the user information on different parameters:

a—Production Information:
1—Generator number
2—Production lot number
3—Production date
4—Production control card.

b—Physical information:
1—Loaded nominal Mo-99 activity.
2—Calibration date and expiration date.
3—Current activity of Mo-99.
4—Hour and date of last elution.
5—Hours elapsed since last elution.
6—Available activity of Tc-99m.
7—Specific activity of Tc-99m expressed in Bq/ng (Ci/ng).

c—Radiopharmacologic information:
1—Instruction on how to use, and care for, the generator, user location, other general recommendations.
2—Available radiopharmaceuticals for use with the eluate of the generator.
3—Labeling techniques of cold radiopharmaceuticals (including kits).

4—Quality Control methods of labeled radiopharmaceuticals

5—Explanatory videos.

6—In the case of a dry Mo-99/Tc-99m generator, the information regarding the residual humidity of the generator is fundamental to secure the next elution, since the elution performance drops drastically in case the generator remains wet. The system guides the user to resolve the problem. If the user fails to log the solution, the generator manufacturer, via internet, may remotely access the data, and call the user to help in resolving the problem.

d—Recordable files:

The program records the following parameters:

1—Generator unit number, lot number, activity

2—Activity, calibration date, date and time of system log-in.

3—Date and time of each elution conducted over the life of the generator.

4—Identification code of the operator performing the elution.

5—Eluted activity.

6—Radionucleidic purity of the Tc-99m obtained (mCi Mo-99/ml Tc-99m).

7—Radiopharmaceuticals labeled with the eluted Tc-99m.

8—Comments by the user.

9—Date and time of log-out from the system.

10—Watchdog: alerts the person in charge of the use of the generator, when the system is connected, and this information may be transmitted to a cellular phone, to a text message reception unit, to a pre-selected message box or e-mail inbox via Internet.

11—Search of performance records of all generators data for statistical analysis or any other usage.

e—Internet Connection:

This connection allows the user to obtain online information for the following parameters of the generator, as these parameters are reported by the manufacturer (sterility and LAL test results are not available for a few days after the generator is shipped to the user):

1—Generator number

2—Production lot number.

3—Production date

4—Production control card

5—Loaded activity

6—Calibration date

7—Quality control card (radiochemical purity, radionucleidic purity, sterility, LAL, etc.)

Furthermore, it allows the producer to obtain information on-line, if access is granted by the user, on the following parameters:

1—Every intervention conducted on the generator.

2—Generator performance.

3—Product use.

4—User profile.

5—Generator traceability during its useful life.

6—Product performance quality in case of discrepancies as to its functioning.

The user has an on-line message box with the producer for comments or suggestions. Such connection allows the functioning of the watchdog described above.

The program runs in the background, using minimum PC capacity, while other functions are being used.

System Configurations and Versions

Example 1

RadioFarma Elucom I System

This system consists of:

A classical Mo-99/Tc-99m generator with either a dry or wet column;

Electronic sensor of elution;

Communication interface by RS 232; USB, parallel port or any other input-output port of a PC; and User interface software.

The system is the most economical and practically does not increase the cost of the generator. It retains all the functions mentioned above, except that there is a lack of electronic memory. It is necessary to input some data manually, namely, lot and generator numbers, so the rest of the information is electronically exchanged with the producer. It neither measures the eluted activity nor the radionucleidic purity of the Tc-99m eluted.

Example 2

RadioFarma Elucom II System

This system consists of:

The classical Mo-99/Tc-99m generator either with a dry or wet column;

Electronic sensor of elution;

On Board electronic memory with information to the user on: lot number, generator number, activity, calibration and expiration dates;

Communication interface by RS 232; USB, parallel port or any other input-output port of a PC; and User interface software.

This version enters the corresponding information of the generator connected to the system, which recognizes it as a new generator and allows electronic exchange of information, notifying the producer that the generator is in place and running.

This version does not measure the eluted activity or the radionucleidic purity of Tc-99m.

Example 3

RadioFarma Elucom III System

This system consists of:

A classical Mo-99/Tc-99m generator with either a dry or wet column;

Electronic sensor of elution;

Electronic memory with information to the user on: lot number, generator number, activity, calibration and expiration dates;

Eluted activity and eluted Tc-99m radionucleidic purity measurement device;

Communication interface by RS 232; USB, parallel port or any other input-output port of a PC; and User interface software.

This version, in addition to all other functions described in previous versions, also provides the on-line measurement of the eluted activity and the radionucleidic purity of Tc-99m. The advantage for the user is the automatic recording of the eluted activity and its radionucleidic purity. The advantage for the producer is the on-line access to this information to check the generator's performance.

System Hardware:

Elution Detection Method:

In addition, this invention provides a method for detecting the elution in the generator, which has several practical alternatives already described.

The sensors used to detect the passage of the liquid through the generator are based on the following physical measurements:

High-frequency conductometry (most used)

Optical intensity

Impedance.

Capacity

Radioactivity

Magnet-hydrodynamic a) High Frequency Conductometry:

It is the method most used and is based on a device having a conductimetric sensor that measures the electrical resistance of a portion of the elution tubing of the generator through which the eluate solution passes. It is clear to those skilled in the art that the conductimetric sensor can be located on other positions of the radioisotope tubings. If the resistance is infinite, it shows that there is no liquid passage and that the column is dry, such condition being ideal for the efficient elution of pertechnetate Tc-99m. A decrease in the electrical resistance, detects the circulating liquid in the elution tubing and the PC logs the moment on which the elution takes place.

If the resistance does not return to infinite, the program reports that the column has residual moisture. This situation should be resolved by inserting another evacuated vial for the purpose of drying the column. If the situation is not resolved after three attempts to dry the column, then the program reports a generator malfunction; and suggests calling the manufacturer for technical support.

b) Optical Intensity:

This device, having an optical sensor, measures changes in the intensity of light which passes by a translucid section of the elution tubing. The signal thus generated is processed as in a).

c) Impedance:

This device, having a free oscillator with a coil over the elution tube, measures the change of the frequency when liquid passes through the elution tube. The signal thus generated is processed as in a).

d) Capacity:

This device, having two electrodes over the elution tube, measures the change of the dielectric capacity when liquid passes through the elution tube. A high-frequency capacitive detector interfaced to the PC makes the detection. The signal thus generated is processed as in a).

e) Activity:

This device measures the activity when the generator is eluted. The measurement may be performed using radioactivity detectors, such as Geiger Müller (GM) tubes, ionization chamber, and proportional detectors, which are solid state detectors known to those skilled in the art. The elution profile of the Tc-99m is recorded in the system's log, together with the following parameters:

1—That the elution is being performed.

2—The eluted activity of the Tc-99m.

3—The measurement of radioactivity without elution gives the activity of Mo-99 remaining in the generator.

4—The second detector protected by 3 mm of lead allows for the determination of the radiochemical purity of the eluted Tc-99m since it detects the quantity of Mo-99 in the elution. If the ratio µCi Mo-99 per mCi Tc-99m is above the limits established by regulations, the Tc-99m shall be discarded, and the information recorded in the system's log.

f) Magnet-Hydrodynamic:

The detection is based on the magnet-hydrodynamic principle, i.e. the generation of a weak orthogonal electric field to the magnetic field applied to the elution pipe of Tc-99m. The measurement of the electric field indicates that the liquid is passing through the interior of the elution tubing.

PC Connection:

It is conducted through RS232, since it is a universal port available in every computer. The use of a port USB, RS422, parallel port connection, etc., is also provided.

ON BOARD Memory:

Such memory is present in versions II and III, and is performed through a non-volatile memory such as EEPROM or equivalent. Said memory, upon connecting the system to the PC transfers to the program all the information relating to the generator: generator number, lot number, loaded activity, calibration date, user etc.

Digital Generator Circuits

Detection Circuits of Liquid Passage:

The following circuits are different variants for the detection of elution of the generator, based on the conductometry detection given by the physiological solution that crosses the column of the generator at the moment of the elution. They are based on a high frequency source (in this case, it is generated by software and a detection amplifier made up of discreet electronics). The communication is given by port RS232 detailed below, but can be made via parallel port, or USB, or joystick port. The equivalence is indicated in the following table. This equivalence is only worth for this particular case and cannot be taken like between-ports equivalence since each one has its own characteristics.

TABLE

| | Port RS232 | | | |
|---|---|---|---|---|
| Name | function | Pin N° DB9 | Pin N° DB25 | Parallel Pin N° |
| DCD | In | 1 | 8 | 11 |
| RXD | In | 2 | 3 | 12 |
| TXD | Out | 3 | 2 | 2 |
| DTR | Out | 4 | 20 | 3 |
| GND | 0 volt | 5 | 7 | 25 |
| DSR | In | 6 | 6 | 13 |
| RTS | Out | 7 | 4 | 4 |
| CTS | In | 8 | 5 | 14 |
| RI | In | 9 | 22 | 15 |

Circuit Number 1: (see FIG. 8)

The identification loop acts to knowledge the program that the circuit was connected to the port. This is the simplest circuit and its operation is as follows: by port RTS, a voltage pulse is sent. If a stop by port RXD is registered, this indicates that the generator is connected to the computer. If the generator is eluting, the Q1 transistor will be placed in short circuit taking the entering pulse by port RTS to mass, detecting a low point in port RXD. In this way, it is detected:

Generator Connected

Generator Eluting

Figure 9:
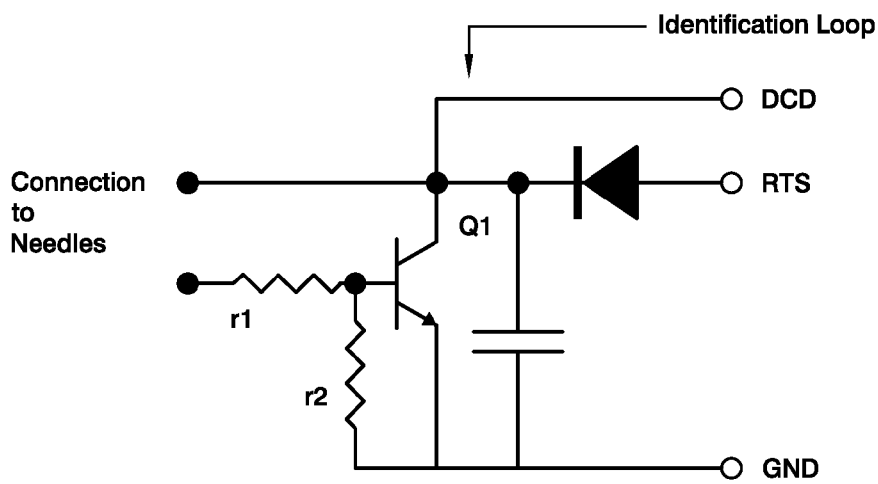
FIG. 9 shows the schematic view of the circuit number 2, working in a similar manner as the previous one but loading the capacitor, whose load is checked by DCD port.

Circuit N° 2: (see FIG. 9)

This circuit works like circuit number 1, but the high pulse entering port RTS loads the capacitor whose load is checked by port DCD. If the generator elutes, Q1 transistor short circuits and discharges the capacitor, being detected from the PC.

Figure 10:
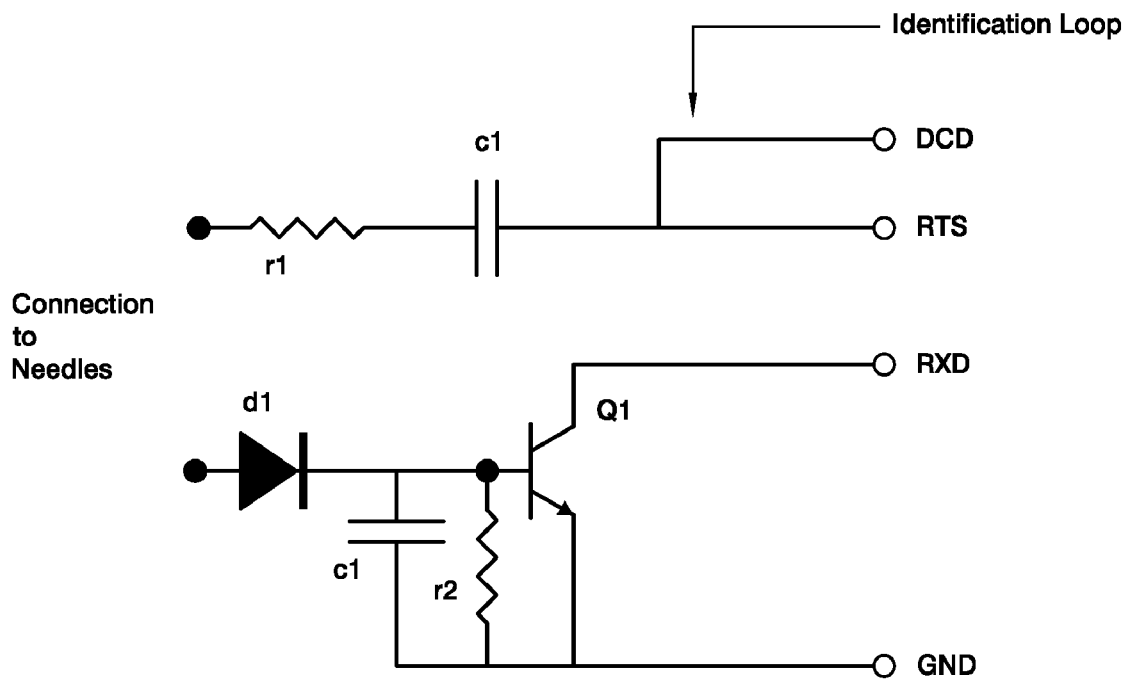
FIG. 10 shows a schematic view of a circuit number 3, which works by circulation of alternate current.

Circuit N° 3: (see FIG. 10)

This circuit works by circulation of alternating current by the "needles connection" loop. The alternating voltage is generated by the PC through port RTS. This is checked by port DCD that verifies the connection of the generator. If the generator elutes activity, it is registered by closing the "needles connection" loop. This closing produces a short circuit in the Q1 transistor producing a low point in port RXD.

Figure 11:
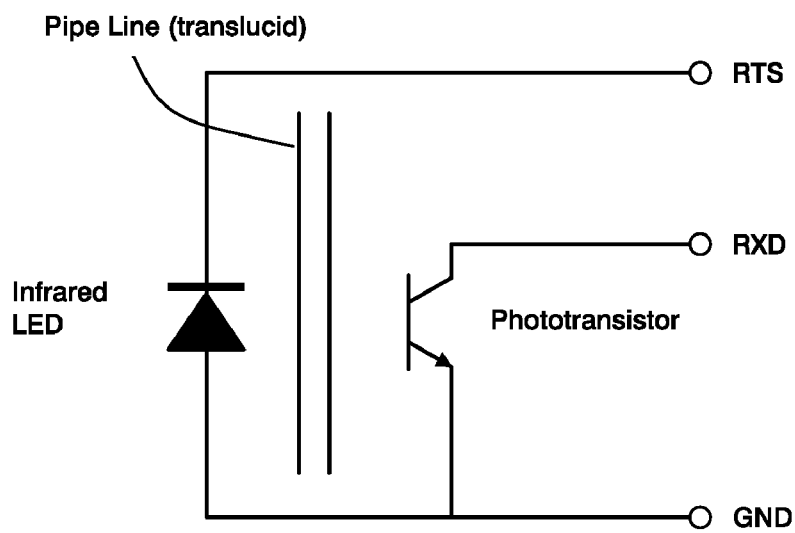
FIG. 11 shows another schematic view of a circuit number 4, which actuates by changes in light intensity.

Detection by optical passage:

Circuit N° 4: (see FIG. 11)

This circuit acts by changes in the light intensity registered by the phototransistor. This change indicates to the program that the generator is eluting, being registered in the file.

Circuit N° 5:(see FIG. 12)

System of USB connection with data registry for Versions 2 and 3; RadioFarma Elucom II system and RadioFarma Elucom III system.

The integrated circuit of Cypress Company is a microprocessor with USB connection that makes possible the interface between the detection circuits of liquid passage and the USB port, allowing recording the information mentioned in "Benefits of the Digital Generator". For the RadioFarma Elucom III system, the circuit has a digital analogical Interface MAX147 that takes data from radioactivity indicators located in different zones of the Mo99-Tc-99 m Generator.

Circuits of Radiation Monitoring: (see FIG. 13)

The RadioFarma Elucom III system has three Geiger Müller-type radiation sensors for measuring the following parameters:

1) Measurement of the remaining Mo-99 activity in the column.
2) Measurement of Tc-99m eluted activity of the generator.
3) Measurement of the radionucleidic purity of the eluted Tc-99m.

These Geiger's are arranged in the generator in the following way:

Geiger N° 1: It measures the remaining Mo-99 activity in the column. It is positioned on the external face of the lead shield of the generator so that the radiation received comes only from the Mo-99 retained in the column.

Geiger N° 2: It measures the activity of the Tc-99m as it is eluted from the generator. It is located in the Tc-99m exit tubing that carries the eluate from the column. When an elution takes place, the activity that circulates in front of this detector is measured and recorded.

Geiger N° 3: It measures the radionucleidic quality of the eluted Tc-99m. It is located 3 mm away from the elution tubing. Between GM N° 3 and the elution tubing there is a 3 mm thick lead shield. Enough Mo-99 gamma radiation (740 KeV) crosses this lead shield to be detected and recorded while the Tc-99m gamma radiation (140 KeV) is totally absorbed and not measured by this detector.

The signals are interfaced to the PC through an 8 channels-12 bits analogical-digital converter, type MAX 147. The data enters the PC via USB port by Cypress C63001 circuit. It is processed by the computer by means of mathematical algorithms giving the following information:

Remaining activity of Mo-99 in the column;

eluted activity of Tc-99m (in case of registering elution);

Radionucleidic purity of Tc-99m in µCi of Mo-99/mCi of Tc-99m; and

Yield of the generator (in % of Tc-99m actually eluted relative to the theoretical value it should have eluted).

We claim:

1. A system to provide performance control of a radioisotope generator, said system comprising:
    a radioisotope generator;
    an electronic sensor of elution;
    an eluted activity measurement sensor;
    means for measuring nuclear quality of the eluted radioisotope;
    an electronic memory with information for a user;
    a communication interface; and
    an user interface software,
    wherein the electronic sensor of elution measures changes in high frequency conductometry.

2. A system according to claim 1, wherein said radioisotope generator is a Mo-99/Tc-99m generator.

3. A system according to claim 2, wherein the means for measuring is comprised of a radioactivity sensor protected by a 3 mm lead shield.

4. A system according to claim 1, wherein the eluted activity sensor is comprised of a Geiger Müller tube, a micro ionization chamber or a solid state detector.

5. A system according to claim 1, wherein the electronic memory with information is comprised of Lot No., Generator No., activity, calibration date and expiration dates.

6. A system according to claim 5, wherein the electronic memory is comprised of a non-volatile memory such as EEPROM, the memory, upon connecting to a PC, transferring information stored by a manufacturer specific to a particular generator.

7. A system according to claim 1, wherein the communication interface uses one or more of the following ports of a PC: RS232, USB, or parallel port.

8. A system according to claim 1, wherein user interface software is able to process and log all data introduced from the generator.

9. A system to provide performance control of a radioisotope generator, said system comprising:
    a radioisotope generator;
    an electronic sensor of elution;
    an eluted activity measurement sensor;
    means for measuring nuclear quality of the eluted radioisotope;
    an electronic memory with information for a user;
    a communication interface; and
    an user interface software,
    wherein the electronic sensor of elution measures changes in photon intensity passing through a portion of elution tubing being transparent to photons.

10. A system according to claim 9, wherein the electronic sensor of elution measures changes in electrical impedance of a portion of elution tubing.

11. A system according to claim 9, wherein the electronic sensor of elution measures changes in dielectric capacity of a portion of elution tubing.

12. A method to detect and measure passage of elution in a radioisotope generator, said method comprising a step from a group consisting of:
    using High-frequency conductometry; using Photometry; using Impedanceometry;
    using Electrical capacitometry; using Emitted radiation detection; or using Magnet-hydrodynamic,
    wherein using high frequency conductometry is comprised of measuring changes in electrical resistance of a portion of elution tubing of the generator.

13. A method according to claim 12, wherein using impendanceometry is comprised of measuring changes in frequency of a free oscillator or rod-capacitor, a coil surrounding a portion of the elution tubing and a free oscillator being connected to the coil; wherein a frequency counter detects impedance changes of the coil if liquid passes through.

14. A method according to claim 12, wherein using capacitometry is comprised of measuring changes in dielectric capacity, two electrodes being placed externally on both sides of a portion of the elution tubing, the tubing being non-metallic with an external diameter of not more than 2 mm, liquid changing an internal dielectric constant of a capacitor formed by the electrodes and the tubing, a capacitometer being connected to the electrodes measuring changes of capacity when liquid passes through the tubing.

15. A method according to claim 12, wherein using emitted radiation detection is comprised of measuring changes in a radiation field generated by the eluted radioisotope passing through the elution tubing of said radioisotope generator, a properly-shielded-from-other-sources-of-radiation radiation detector being placed against said elution tubing of said radioisotope generator.

16. A method according to claim 12, wherein using magnet-hydrodynamic is comprised of changes to an orthogonal electric field generated by a magnetic field applied to elution tubing, a magnetic field being applied on a portion of the elution tubing, two electrodes orthogonal to the magnetic field measuring a low electric field that is a function of the liquid flow, and when the liquid passes through the tubing, the electric field increasing and indicating elution.

17. A method according to claim 12, for measuring dryness of a "dry" Mo-99/Tc-99m generator, said method further comprising the steps of:
using high frequency conductometry to measure changes in electrical resistance through a column, electrodes being placed on an end and an opposite end of metal tubing or needles of the generator.

18. A method according to claim 12, for detecting and measuring the radionucleidic purity of the Tc-99m as eluted from a Mo-99/Tc-99m generator, said method comprising the steps of:
measuring changes in a radiation field generated by eluted radioisotope passing through elution tubing of the radioisotope generator, a second properly-shielded-from-other-sources-of-radiation radiation detector being placed against a 3 mm thick lead shield, in direct contact with said elution tubing of said radioisotope generator.

19. A method to transmit the data generated according to claim 12, further comprising:
transmitting data to a PC or data processor through a RS232 or USB or a parallel port or any other input-output port of a PC.

20. A method to detect and measure passage of elution in a radioisotope generator, said method comprising a step from a group consisting of:
using High-frequency conductometry; using Photometry; using Impedanceometry; using Electrical capacitometry; using Emitted radiation detection; or using Magnet-hydrodynamic,
wherein using photometry is comprised of measuring changes in intensity of a light beam going through a translucent portion of elution tubing, a high intensity light emitter being pointed to the translucent portion of the elution tubing, a phototube/photomultiplier being placed on an other side of the translucent portion of said elution tubing of said radioisotope generator, being directly opposite to the light emitter.

21. A method according to claim 20, for detecting and measuring the radionucleidic purity of the Tc-99m as eluted from a Mo-99/Tc-99m generator, said method comprising the steps of:
measuring changes in a radiation field generated by eluted radioisotope passing through elution tubing of the radioisotope generator, a second properly-shielded-from-other-sources-of-radiation radiation detector being placed against a 3 mm thick lead shield, in direct contact with said elution tubing of said radioisotope generator.

22. A method to transmit the data generated according to claim 20, further comprising:
transmitting data to a PC or data processor through a RS232 or USB or a parallel port or any other input-output port of a PC.

* * * * *